US008999925B2

(12) United States Patent
Spence et al.

(10) Patent No.: US 8,999,925 B2
(45) Date of Patent: Apr. 7, 2015

(54) ARENAVIRUS INHIBITING PEPTIDES AND USES THEREFOR

(71) Applicant: The Administrators of the Tulane Educational Fund, New Orleans, LA (US)

(72) Inventors: Jennifer S. Spence, New Orleans, LA (US); Robert F. Garry, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 13/828,581

(22) Filed: Mar. 14, 2013

(65) Prior Publication Data

US 2014/0243256 A1     Aug. 28, 2014

Related U.S. Application Data

(60) Provisional application No. 61/769,656, filed on Feb. 26, 2013.

(51) Int. Cl.
| | | |
|---|---|---|
| *A61K 38/08* | (2006.01) | |
| *A61K 38/10* | (2006.01) | |
| *A61K 38/16* | (2006.01) | |
| *C07K 7/06* | (2006.01) | |
| *C07K 7/08* | (2006.01) | |
| *C07K 14/08* | (2006.01) | |

(52) U.S. Cl.
CPC . *C07K 14/08* (2013.01); *C07K 7/06* (2013.01); *C07K 7/08* (2013.01); *C12N 2760/10033* (2013.01); *Y10S 530/826* (2013.01)

(58) Field of Classification Search
None
See application file for complete search history.

(56) References Cited

U.S. PATENT DOCUMENTS

| | | | | |
|---|---|---|---|---|
| 6,150,168 | A * | 11/2000 | Woo et al. | 435/440 |
| 6,417,326 | B1 * | 7/2002 | Cullis et al. | 530/324 |
| 2009/0264362 | A1 * | 10/2009 | Garry et al. | 514/12 |
| 2010/0261640 | A1 * | 10/2010 | Branco et al. | 514/3.7 |
| 2013/0039948 | A1 * | 2/2013 | Sigalov | 424/278.1 |

FOREIGN PATENT DOCUMENTS

WO        WO 0220053 A1 *  3/2002

OTHER PUBLICATIONS

Hrobowski, Y.M. et al., Peptide Inhibitors of Dengue Virus and West Nile Virus Infectivity, Virology Journal, vol. 2 (49), (2005).
St. J. Jones, P.L. et al., Conformational Changes in Cell Surface HIV-1 Envelope Glycoproteins Are Triggered by Cooperation Between Cell Surface CD4 and Co-Receptors, The Journal of Biological Chemistry, vol. 273 (1), 404-409 (1998).
Chu, V.C. et al., The Avian Coronavirus Infectious Bronchitis Virus Undergoes Direct Low-pH-Dependent Fusion Activation During Entry Into Host Cells, Journal of Virology, vol. 80 (7), 3180-3188 (2006).
Hoekstra, D. et al., Fluorescence Method for Measuring the Kinetics of Fusion Between Biological Membranes, Biochemistry, vol. 23, 5675-5681 (1984).
Niaid, Biodefense Research Agenda for CDC Category A Agents, National Institute of Health, Publication No. 03-5308, Bethseda, MD (2002).
Carr, C.M. et al., Influenza Hemagglutinin is Spring-Loaded by a Metastable Native Conformation, Proc. Natl. Acad. Sci., vol. 94, 14306-14313 (1997).
Gaspar, L.P. et al., Hydrostatic Pressure Induces the Fusion-Active State of Enveloped Viruses, The Journal of Biological Chemistry, vol. 277 (10), 8433-8439 (2002).
Eschli, B. et al., Identification of an N-Terminal Trimeric Coiled-Coil Core Within Arenavirus Glycoprotein 2 Permits Assignment to Class I Viral Fusion Proteins, Journal of Virology, vol. 80 (12), 5897-5907 (2006).
Sainz, B., Jr. et al., Inhibition of Severe Acute Respiratory Syndrome-Associated Coronavirus (SARS-CoV) Infectivity by Peptides Analogous to the Viral Spike Protein, Virus Research, vol. 20, 146-155 (2006).
Neuman, B.W. et al., Complementarity in the Supramolecular Design of Arenaviruses and Retroviruses Revealed by Electron Cryomicroscopy and Image Analysis, Journal of Virology, vol. 79 (6), 3822-3830, (2005).
Neuman, B.W. et al., Purification and Electron Cryomicroscopy of Coronavirus Particles, Methods in Molecular Biology, SARS-and Other Coronaviruses, vol. 454, 129-136 (2008).
Wimley, W.C. et al., Experimentally Determined Hydrophobicity Scale for Proteins at Membrane Interfaces, Nature Structural Biology, vol. 3 (10), 842-848 (1996).
Di Simone, C. et al., Virology, vol. 198, 455-465 (1994).
Weber, G. et al., Fluorescent Indicators of Adsorption in Aqueous Solution and on the Solid Phase, Proceedings of the Biochemical Journal 56 (325th Meeting): xxxi, d-2 (1954).

* cited by examiner

*Primary Examiner* — Jeffrey E Russel
(74) *Attorney, Agent, or Firm* — Olson & Cepuritis, Ltd.

(57) ABSTRACT

The present invention describes peptides which inhibit fusion of an arenavirus (e.g., Pichinde virus; PICV) with a host cell membrane. The arenavirus inhibiting (AVI) peptides described herein comprise a segment of the GP2 protein of an arenavirus. The AVI peptides are useful for inhibiting arenavirus-to-host cell membrane fusion and for treating arenavirus infections. In a particular embodiment, the arenavirus inhibiting peptide comprises a segment of PICV glycoprotein 2 (PICV GP2; SEQ ID NO: 1), Tamiami virus (TAMV) GP2 (SEQ ID NO: 14), or Lassa virus (LASV) GP2 (SEQ ID NO: 15). In particular, the segment is selected from a region of an arenavirus GP2 extending from the N-terminus into the first half of the FIR (i.e., from residues 1 through 105 of SEQ ID NO: 1, SEQ ID NO: 14, or SEQ ID NO: 15).

20 Claims, 8 Drawing Sheets

Formatted Alignments

```
                                                              20
Pichinde virus GP2 sequence   G F P T W D L S D S   S G Q H   V P G G Y C L E Q W A I I W A G
Tamiami virus GP2             S F P T W S L S D A   V G N D   M P G G Y C L E K W M L V - A S
Lassa virus GP2               G T F T W T L S D S   E G N A   T P G G Y C L T R W M L I E A E 40                                  60
Pichinde virus GP2 sequence   - I K C F D N T V M A K C N K   D H N   E E F C D T M R L F D F
Tamiami virus GP2             Q L K C F G N T A Y A K C N L   N H D S R F C D M L R L F D F
Lassa virus GP2               - I K C F G N T A V A K C N E K H D E E F C D M L R L F D F 80
Pichinde virus GP2 sequence   N Q N A I K T L Q L N   V E N - S - L N L F K K T I N G L L S
Tamiami virus GP2             N E K A I E T L Q - N K T R - S Q E N I A I N A I N S L I S
Lassa virus GP2               N Q Q A I S R K K - S E A Q M S - L Q L I N K A V N A L I N 100                               120
Pichinde virus GP2 sequence   D S L V I R N S L K Q L A K I P Y C N Y T K F W Y I N D T -
Tamiami virus GP2             D N L L M K N R L K E L M D I P F C N Y T K F W Y V N H T K
Lassa virus GP2               D Q L I M K N H L R D I M G I P Y C N Y S K Y W Y L N H T -

140
Pichinde virus GP2 sequence   I T G R H S L P Q C W L V H N G S Y L N E T H F K N D W L -
Tamiami virus GP2             L N - H H S L P R C W L V K N G S Y L N E S E F R N D W L -
Lassa virus GP2               I T G R T S L P R C W L V S N G S Y L N E T H F S D D - L E 160                    180
Pichinde virus GP2 sequence   W E S Q N L Y N E M L M K E Y E E R Q G K T P L A L T D I C
Tamiami virus GP2             L E S D H L I S E I L S K E Y E E R Q G R T P L S L V - I C
Lassa virus GP2               Q Q A D N M I T E M L Q K E Y M E R Q G K T P L G L V D L -

200
Pichinde virus GP2 sequence   F - W S L V P Y T I T V F L H I V G I P T H R H I I G D Q C
Tamiami virus GP2             F - W S T L P Y T A S I F L H L I R I P T H R H I T G E Q C
Lassa virus GP2               F V F S T S F Y L I S I F L H L V K I P T H R H I V G K P C 220                    240
Pichinde virus GP2 sequence   P K P H R I T R N L C S C G Y Y K Y Q - R N - - L - - -
Tamiami virus GP2             P K P H R L K A D S T C A C G L Y K - Q K R R - P I N W V E
Lassa virus GP2               P K P H R L N H M G I C S C G L Y K - Q - P G V P V R W -

260
Pichinde virus GP2 sequence   T N G
Tamiami virus GP2             S N - -
Lassa virus GP2               K R - -
```

US 8,999,925 B2

ARENAVIRUS INHIBITING PEPTIDES AND USES THEREFOR

CROSS-REFERENCE TO RELATED APPLICATIONS

This application claims priority to provisional application U.S. Application. Ser. No. 61/769,656 filed Feb. 26, 2013, which is incorporated herein by reference in its entirety.

STATEMENT OF GOVERNMENT SUPPORT

A portion of the work described herein was supported by funding grant number 1U01AI082119 from the National Institute of Health. The United States government has certain rights in this invention.

INCORPORATION OF SEQUENCE LISTING

Biological sequence information for this application is included in an ASCII text file having the file name "TU497SEQ.txt," created on Mar. 11, 2013, and having a file size of 9,708 bytes, which is incorporated herein by reference.

FIELD OF THE INVENTION

The present invention relates to compositions comprising peptides effective for preventing or inhibiting viral infection of a cell by an arenavirus, and to methods of treating or preventing arenavirus infections with the peptide.

BACKGROUND OF THE INVENTION

All viruses must bind to and invade their target cells to replicate. For enveloped animal viruses, including RNA viruses having Class I membrane fusion proteins (Type I viruses), the process involves (a) binding of the virion to the target cell, (b) fusion of the envelope of the virus with the plasma membrane or an internal cellular membrane, (c) destabilization of the viral envelope and cellular membrane at the fused area to create a fusion pore, (d) transfer of the viral RNA through the pore, and (e) modification of cellular function by the viral RNA.

Fusion of the viral membrane and the cell envelope, steps (b) and (c) above, is mediated by the interaction of a viral transmembrane glycoprotein (fusion protein) with surface proteins and membranes of the target cell. These interactions cause conformational changes in the fusion protein that result in the insertion of a viral fusion peptide into the target cell membrane. This insertion is followed by further conformational changes within the fusion protein that bring the viral envelope and cell membranes into close proximity and results in the fusion of the two membrane bilayers.

Identification of classes of RNA Type I viruses and fusion proteins and methods of inhibiting the function of the fusion initiation region in RNA viruses are described in PCT/US2004/036578, filed Nov. 3, 2004, and U.S. application Ser. No. 12/452,240, filed Dec. 22, 2009, each of which is incorporated herein by reference in its entirety.

The Arenaviridae family of enveloped, negative-stranded RNA viruses encompasses a number of hemorrhagic fever (HF) viruses, five of which have been designated category A agents by the CDC and NIAID. Lassa virus (LASV) is the most prevalent of the HF viruses, with approximately 500,000 cases estimated annually in West Africa. Outbreaks of arenavirus HF occur sporadically in South America, as well, and mortality rates in hospitalized cases can exceed 40%. Clinical treatment of arenavirus infection is currently limited to administration of the nucleoside analogue ribavirin, which is marked by significant toxicity and sub-optimal efficacy.

Arenavirus infection is initiated by its glycoprotein complex (GPC), which is expressed as a polypeptide and cleaved into three segments by a signal peptidase and SKI-1/S1P. The mature glycoprotein spike consists of a receptor-binding subunit (GP1), a membrane-anchored fusion protein (GP2), and a unique signal peptide. At 58 amino acids in length, the arenavirus signal peptide is 2-4 times longer than most viral signal peptides. It features two transmembrane domains and remains associated with GP2, with a possible role in spike stability.

The Arenavirus GP2 is considered a class I viral fusion protein on the basis of its α-helical major domains. Following receptor binding and endocytosis, the decreased pH disrupts GPC intermolecular and intramolecular bonds. Dissociation of GP1 exposes the fusion peptide region of GP2, which can insert into the endosomal membrane. Virus-cell fusion is mediated by the rearrangement of GP2 trimers into a lower-energy conformation, the six-helical bundle (6-HB), bringing together the viral and endosomal bilayers. The entry process represents a potential target for antiviral agents, one of the most notable entry inhibitors being the HIV drug enfuvirtide. Derived from the C-terminal heptad repeat (CHR) of HIV gp41, enfuvirtide is a peptide inhibitor of viral fusion and prevents stable 6-HB formation. Fusion inhibitors of similar design have been reported for coronaviruses, flaviviruses, orthomyxoviruses, paramyxoviruses, and filoviruses. Peptide drugs generally possess high specificity and low toxicity.

There is an ongoing need for peptide drugs and methods for treating arenavirus infections. The peptide, compositions, and methods described herein address this need.

SUMMARY OF THE INVENTION

As described herein, peptides derived from the N-terminal heptad repeat (NHR) of Pichinde virus (PICV) GP2 (SEQ ID NO: 1) are demonstrated to inhibit infection specifically by Old and New World arenaviruses by a novel mechanism. The present invention describes peptides which inhibit fusion of an arenavirus (e.g., Pichinde virus, Lassa virus, and Tamiami virus) with a host cell membrane. The arenavirus inhibiting (AVI) peptides described herein comprise a segment of the GP2 protein of an arenavirus. The AVI peptides are useful for inhibiting arenavirus-to-host cell membrane fusion and for treating arenavirus infections. In a particular embodiment, the arenavirus inhibiting peptide comprises a segment of PICV glycoprotein 2 (PICV GP2; SEQ ID NO: 1), Tamiami virus (TAMV) GP2 (SEQ ID NO: 14), or Lassa virus (LASV) GP2 (SEQ ID NO: 15). In particular, the segment is selected from a region of an arenavirus GP2 extending from the N-terminus into the first half of the fusion initiation region (FIR) (i.e., from residues 1 through 105 of SEQ ID NO: 1, SEQ ID NO: 14, or SEQ ID NO: 15). In some preferred embodiments, the selected segment of GP2 includes no more than 2 to 4 residues of the FIR, or no residues from the FIR. For example, the segment can be from the region of residues 1 to 96 or residues 1 to 94 of SEQ ID NO: 1, SEQ ID NO: 14 or SEQ ID NO: 15.

In one preferred embodiment, the AVI peptide consists of 9 to 50 consecutive amino acid residues from the designated portion of PICV GP2 (i.e., from residues 1 to 105 of SEQ ID NO: 1), more preferably 9 to 40, 9 to 30, or 15 to 20 consecutive amino acid residues from the region of residues 1 to 105 of SEQ ID NO: 1. Preferably, the segment of the PICV GP2 comprises at least residues 75 to 93 of SEQ ID NO: 1 (i.e., corresponding to SEQ ID NO: 4, also referred to herein as "Peptide 1"). The segment can include one or more substitutions to replace a cysteine residue with alanine or substitution of a serine residue with glutamine (e.g., to prevent oxidative dimerization of cysteine residues, to improve the solubility of the peptide, or affect the alpha-helical potential of the peptide).

The following embodiments illustrate certain preferred features and aspects of the AVI peptides and their uses described herein.

Embodiment 1 comprises arenavirus fusion inhibiting (AVI) peptide having an amino acid sequence consisting of a 9 to 50 consecutive amino acid residue segment of SEQ ID NO: 1, SEQ ID NO: 14, or SEQ ID NO: 15 from the region of residues 1 to 105 (or residues 1 to 96, or residues 1 to 94) thereof; wherein optionally, a cysteine residue of the segment of SEQ ID NO: 1, SEQ ID NO: 14, or SEQ ID NO: 15 is replaced by an alanine residue, and optionally, a serine residue of the segment of SEQ ID NO: 1, SEQ ID NO: 14, or SEQ ID NO: 15 is replaced by a glutamine residue.

Embodiment 2 comprises the AVI peptide of embodiment 1 wherein the 9 to 50 consecutive amino acid residue segment includes at least consecutive residues 75 to 93 of SEQ ID NO: 1.

Embodiment 3 comprises the AVI peptide of embodiment 1 or embodiment 2 wherein the amino acid sequence of the peptide consists of 15 to 20 consecutive amino acid residues from the designated region of SEQ ID NO: 1, SEQ ID NO: 14, or SEQ ID NO: 15.

Embodiment 4 comprises the AVI peptide of embodiment 1 wherein the amino acid sequence of the peptide consists of SEQ ID NO: 4.

Embodiment 5 comprises the AVI peptide of embodiment 1 wherein the amino acid sequence of the peptide consists of a sequence selected from the group consisting of SEQ ID NO: 5 to SEQ ID NO: 11, inclusive.

Embodiment 6 comprises AVI peptide of any one of embodiments 1 to 5 for use in treating an arenavirus infection.

Embodiment 7 comprises the AVI peptide of any one of embodiments 1 to 5 for use in inhibiting arenavirus-to-host cell membrane fusion.

Embodiment 8 comprises the AVI peptide of embodiment 6 or embodiment 7 wherein the arenavirus Pichinde virus (PICV), Tamiami virus, or Lassa virus.

Embodiment 9 comprises a pharmaceutical composition comprising the arenavirus fusion inhibiting peptide of any one of embodiments 1 to 8 in a pharmaceutically acceptable carrier.

Embodiment 10 comprises the pharmaceutical composition of embodiment 9 wherein the pharmaceutically acceptable carrier comprises an aqueous buffer at a pH of about 6.5 to 7.5 (i.e., a physiological pH).

Embodiment 11 comprises the pharmaceutical composition of embodiment 9 or embodiment 10 wherein the pharmaceutically acceptable carrier comprises physiological saline solution (i.e., 0.9% (w/v) aqueous sodium chloride).

Embodiment 12 comprises the pharmaceutical composition of any one of embodiments 9 to 11 wherein the pharmaceutically acceptable carrier comprises phosphate buffered saline.

Embodiment 13 comprises the pharmaceutical composition of embodiment 9 wherein the pharmaceutically acceptable carrier comprises a buffer salt and the composition is a spray dried or lyophilized powder.

Embodiment 14 comprises the pharmaceutical composition of embodiment 13 wherein the pharmaceutically acceptable carrier comprises a water soluble sugar or sugar alcohol (e.g. mannitol).

Embodiment 15 comprises a method of treating an arenavirus infection comprising administering an effective amount of an arenavirus fusion inhibiting peptide of any one of embodiments 1 to 8 to a subject.

Embodiment 16 comprises use of an arenavirus fusion inhibiting peptide of any one of embodiments 1 to 8 to treat an arenavirus infection.

Embodiment 17 comprises use of an arenavirus fusion inhibiting peptide of any one of embodiment 1 to 8 for the preparation of a medicament for treating an arenavirus infection.

Embodiment 18 comprises the use of embodiment 16 or embodiment 17 wherein the arenavirus is Pichinde virus (PICV), Tamiami virus (TAMV), or Lassa virus (LASV).

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BRIEF DESCRIPTION OF THE FIGURES

FIG. 5 is a line graph showing peptide-induced dequenching of R18-labeled PICV.

FIG. 6 is a cryo-electron micrograph of untreated PICV.

FIG. 14 shows formatted alignments of Pichinde virus GP2 (SEQ ID NO: 1), Tamiami virus GP2 (SEQ ID NO: 14), and Lassa virus GP2 (SEQ ID NO: 15).

DETAILED DESCRIPTION OF THE INVENTION

Figure 1:
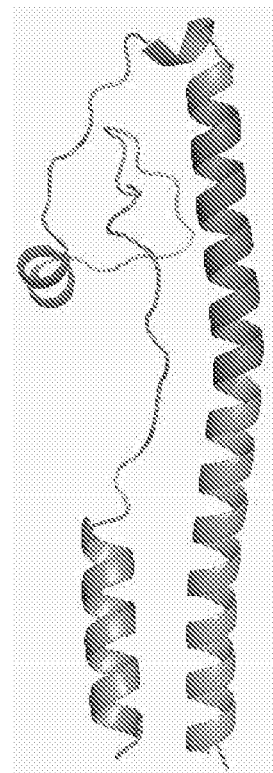
FIG. 1 shows the location of the AVI peptide sequence of SEQ ID NO: 4 (Peptide 1) in Pymol rendering of the PICV GP2 ectodomain.

PICV GP2 is a 230 amino acid long protein having the amino acid sequence: GFFTWDLSDSSGQHVPGGY- CLEQWAIIWAGIKCFDNTVMAKCNKDH-
NEEFCDTMRLFD FNQNAIKTLQLNVENSLNLFKK-
TINGLISDSLVIRNSLKQLAKIPYCNYTKFWYINDTITG
RHSLPQCWLVHNGSYLNETHFKNDWL-
WESQNLYNEMLMKEYEERQGKTPLALTDICF WSLV-
FYTITVFLHIVGIPTHRHIIGDGCPK-
PHRITRNSLCSCGYYKYQRNLTNG (SEQ ID NO: 1). The fusion peptide region of PICV GP2 has the amino acid sequence of: GFFTWDLSDSSGQHVPGGY (SEQ ID NO: 2), corresponding to residues 1 to 19 of SEQ ID NO: 1. The FIR of PICV GP2 has the amino acid sequence of: SLKQLAKIPYCNYTKFWYINDTITGRHSLPQC (SEQ ID NO: 3), corresponding to residues 95 to 126 of SEQ ID NO: 1. FIG. 14 shows the highly conserved nature of the GP2 proteins of three arenaviruses Pichinde virus, Tamiami virus, and Lassa virus.

The arenavirus inhibiting peptides described herein are derived from roughly the N-terminal half of the PICV GP2, TAMV GP2, or LASV GP2 protein. An AVI peptide as described herein has an amino acid sequence consisting of a 9 to 50 consecutive amino acid residue segment (e.g., 9 to 30 consecutive amino acid residues, or 15 to 20 consecutive amino acid residues) from the region of residues 1 to 105 of SEQ ID NO: 1, SEQ ID NO: 14, or SEQ ID NO: 15; wherein optionally, a cysteine residue of the segment is replaced by an alanine residue, and optionally, a serine residue of the segment is replaced by a glutamine residue. The AVI peptides inhibit fusion of an arenavirus, such as Pichinde virus, Tamiami virus, or Lassa virus.

Pharmaceutical Preparations

The instant invention also provides pharmaceutical preparations which contain a pharmaceutically effective amount of the peptides in a pharmaceutically acceptable carrier (e.g., a diluent, complexing agent, additive, excipient, adjuvant and the like). The peptide can be present for example in a salt form, a micro-crystal form, a nano-crystal form, a co-crystal form, a nanoparticle form, a microparticle form, or an amphiphilic form. The carrier can be an organic or inorganic carrier that is suitable for external, enteral or parenteral applications. The peptides of the present invention can be compounded, for example, with the usual non-toxic, pharmaceutically acceptable carriers for tablets, pellets, capsules, liposomes, suppositories, intranasal sprays, solutions, emulsions, suspensions, aerosols, targeted chemical delivery systems, and any other form suitable for use. Non-limiting examples of carriers that can be used include water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, liquid or aerosol form. In addition auxiliary, stabilizing, thickening and coloring agents and perfumes can be used.

In some embodiments, the pharmaceutical compositions include, but are not limited to, those forms suitable for oral, rectal, nasal, parenteral (including intramuscular, subcutaneous, and intravenous), spinal (epidural, intrathecal), and central (intracerebroventricular) administration. The compositions can, where appropriate, be conveniently provided in discrete dosage units. The pharmaceutical compositions of the invention can be prepared by any of the methods well known in the pharmaceutical arts. Some preferred modes of administration include intravenous (iv), subcutaneous, oral and spinal.

Pharmaceutical formulations suitable for oral administration include capsules, cachets, or tablets, each containing a predetermined amount of one or more of the peptides, as a powder or granules. In another embodiment, the oral composition is a solution, a suspension, or an emulsion. Alternatively, the peptides can be provided as a bolus, electuary, or paste. Tablets and capsules for oral administration can contain conventional excipients such as binding agents, fillers, lubricants, disintegrants, colorants, flavoring agents, preservatives, or wetting agents. The tablets can be coated according to methods well known in the art, if desired. Oral liquid preparations include, for example, aqueous or oily suspensions, solutions, emulsions, syrups, or elixirs. Alternatively, the compositions can be provided as a dry product for constitution with water or another suitable vehicle before use. Such liquid preparations can contain conventional additives such as suspending agents, emulsifying agents, non-aqueous vehicles (which may include edible oils), preservatives, and the like. The additives, excipients, and the like typically will be included in the compositions for oral administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Pharmaceutical compositions for parenteral, spinal, or central administration (e.g. by bolus injection or continuous infusion) or injection into amniotic fluid can be provided in unit dose form in ampoules, pre-filled syringes, small volume infusion, or in multi-dose containers, and preferably include an added preservative. The compositions for parenteral administration can be suspensions, solutions, or emulsions, and can contain excipients such as suspending agents, stabilizing agents, and dispersing agents. Alternatively, the peptides can be provided in powder form, obtained by aseptic isolation of sterile solid or by lyophilization from solution, for constitution with a suitable vehicle, e.g. sterile, pyrogen-free water, before use. The additives, excipients, and the like typically will be included in the compositions for parenteral administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 100 millimolar, preferably at least about 1 nanomolar to about 10 millimolar.

Pharmaceutical compositions suitable for intra-nasal administration are also encompassed by the present invention. Such intra-nasal compositions comprise a peptide of the invention in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the peptide. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the peptide. Alternatively, pharmaceutical compositions for administration by inhalation or insufflation can be provided in the form of a dry powder composition, for example, a powder mix of the peptide and a suitable powder base such as lactose or starch. Such powder composition can be provided in unit dosage form, for example, in capsules, cartridges, gelatin packs, or blister packs, from which the powder can be administered with the aid of an inhalator or insufflator. The additives, excipients, and the like typically will be included in the compositions of intra-nasal administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Optionally, the pharmaceutical compositions of the present invention can include one or more other therapeutic agents, e.g., as a combination therapy. The additional therapeutic agent will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with a peptide of the present invention.

As used herein, a "therapeutically effective dosage" or "effective amount" refers to a dosage (e.g., about 1 microgram per kilogram to about 10 mg per kilogram) of the peptide such that when administered results in prevention of infection or mitigation of the symptoms of infection. The dosage and number of doses (e.g. single or multiple dose) administered to a subject will vary depending upon a variety of factors, including the route of administration, patient conditions and characteristics (sex, age, body weight, health, size), extent of symptoms, concurrent treatments, frequency of treatment and the effect desired, the concentration of plasmids in the composition, and the like. Adjustment and manipulation of dosage ranges, as well as in vitro and in vivo methods of determining the therapeutic effectiveness of the composition in an individual, are well within the ability of those of ordinary skill in the medical arts.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The following examples are provided to illustrate certain aspects of the peptides and methods described herein.

Example 1

Materials and Methods

Peptides.

Membrane Protein Explorer (website address http(://)blanco.biomol.uci(.)edu/mpex/) was used to predict GPC regions/sequences involved in intramolecular interface formation. Peptides were synthesized by BioSynthesis (Lewisville, Tex.). Lyophilized peptides were resuspended in dimethyl sulfoxide (DMSO) as 5 mM stock solutions.

Cells and Viruses.

Vero cells (ATCC, Manassas, Va.) for plaque assays were maintained in Dulbecco's modified Eagle medium (DMEM) with 10% fetal bovine serum (FBS), 100 U/mL penicillin, and 100 mg/mL streptomycin.

PICV (CoAn 3739), Tamiami virus (TAMV), vesicular stomatitis virus (VSV), and pseudotyped VSV expressing LASV GPC (VSVΔLASV), herpes simplex virus-1 (HSV-1, McIntyre strain), and measles virus (MV) were obtained from T. Voss at the Tulane University School of Medicine. Viruses were propagated in Vero cells in DMEM with 1% FBS until cytopathic effects were observed (2-6 days). The supernatants were clarified by centrifugation at 1500×g for 5 minutes (m), and aliquots were stored at −80° C.

Plaque Reduction Inhibition Assay.

Vero cells were seeded at a density of $2.75\times10^5$ cells/well in 12-well plates and incubated 24 hours (h) to produce confluent monolayers. Viruses (50 plaque-forming units/well) were incubated in serum-free DMEM for 1 hour at 37° C. with peptide concentrations as indicated for each experiment. Virus-peptide inocula were added to washed monolayers and allowed to adsorb for 1 h at 37° C. prior to removal. Monolayers were overlaid with 2% methylcellulose (VSV, VSVΔ-LASV, HSV-1, and MV) or 1.2% avicel (PICV and TAMV) in DMEM with 1% FBS, 100 U/mL penicillin, and 100 mg/mL streptomycin. Plates were incubated 2 (VSV), 3 (VSVΔ-LASV, HSV-1), 4 (MV), 6 (PICV), or 8 (TAMV) days at 37° C. After overlay removal, monolayers were washed, fixed with 4% buffered formalin, and stained with crystal violet. Statistical analyses were carried out using PRISM software.

Virus Purification.

PICV was purified by methods adapted from Neuman et al. Protein was precipitated from clarified supernatant by the addition of 10% PEG-8000 (w/v) and 1% NaCl (w/v) with gentle stirring overnight at 4° C. Following centrifugation at 10,000×g for 30 min at 4° C., pellets were resuspended in PBS, and then virus was further purified through a 10-20-30% sucrose gradient at 100,000×g for 90 minutes (m) at 4° C. Protein was solubilized in PBS at an approximate concentration of 2 mg/mL and stored as 100 μg aliquots at −80° C.

Liposome Preparation.

1-palmitoyl-2-oleoyl-sn-glycero-3-phosphocholine (POPC, Avanti Polar Lipids) in chloroform was evaporated under nitrogen stream and lyophilized overnight to remove all traces of solvent. The lipid film was hydrated with PBS to a POPC concentration of 10 mM. Large unilamellar vesicles (LUV) were formed by extrusion under nitrogen pressure through two stacked 0.4 mm polycarbonate membranes (Nuclepore) followed by extrusion through two stacked 0.1 mm membranes (the latter step repeated a total of ten times) in an extruder.

Virus-Liposome Fusion Assay.

Octadecyl rhodamine B chloride (R18) in ethanol was added to 100 µL aliquots of purified PICV (1 mg/mL in PBS) at a concentration of 100 nM. The solution was gently shaken in the dark at room temperature for 1 h prior to use to ensure complete uptake of the label. This concentration of R18 enabled self-quenching of the dye in viral membranes with no measurable free dye in solution, thereby obviating additional processing. For the assays, 10 µg labeled viral protein were incubated for 1 h with peptide in PBS. Liposomes were added to a concentration of 100 µM POPC. The solution was acidified by the addition of pre-determined volumes of 1 or 0.1 N HCl with a five minute incubation period between measurements. Total dilution of the PICV-peptide solution did not exceed 5%. Final volume in the cuvette was 250 µL. Complete dequenching of dye was achieved by the addition of 1% Triton X-100 (v/v). Assays were performed in a SLM-Aminco (Urbana, Ill.) fluorescence spectrophotometer thermostatted at 37° C., 8 cm slit width. Fluorescence emission spectra were obtained over 565-635 nm with fixed excitation at 555 nm. Spectra are presented as the averages of three scans. Percentage dequenching at 582 nm was calculated by: $100(F_t-F_0)/(F_{Triton}-F_0)$.

Steady-State Fluorescence Anisotropy Measurements/Assay.

1,6-Diphenylhexatriene (DPH) or 1-(4-trimethylammoniumphenyl)-6-phenyl-1,3,5-hexatriene p-toluenesulfonate (TMA-DPH) was incorporated into POPC LUVs at a 1:100 molar ratio or into purified PICV at a ratio of 3.3 pmol per 1 µg viral protein. The probes were incorporated into membranes by 90 min incubation at RT in the dark. Final probe concentrations were 1 µM in 100 µM POPC and 400 nM in 30 µg PICV. Labeled LUVs or virions were incubated 10 min with peptide prior to measurements. Assays were performed at 37° C., and final cuvette volume was 250 µL. Fluorescence emission spectra were obtained over 400-600 nm with fixed excitation at 395 nm. L-configuration polarization was used. Anisotropy (r) was calculated by the instrument's software using the equation: $r=I_{Vv}-GI_{Vh}/I_{Vv}+2GI_{Vh}$, where $I_{Vv}$ and $I_{Vh}$ are the intensities of the emitted polarized light with the emission polarizer parallel or perpendicular, respectively, to the excitation polarizer, and G ($G=I_{Hv}/I_{Hh}$) is the correction factor.

Cryo-Electron Microscopy.

Purified PICV in PBS was incubated with 0.1 NHCL or peptide for 1 h at 37° C. then UV-irradiated for 30 min. Final concentration of viral protein was 1 mg/mL. Approximately 3-5 µL solution were adsorbed onto lacy carbon film 200-mesh copper grids (Electron Microscopy Sciences, Hatfield Pa.), blotted, and plunged into liquid ethane using a VITROBOT Mark IV (FEI). Samples were imaged with a Tecnai G2 F30 TWIN transmission electron microscope (FEI) at 150 keV under low dose conditions.

Crosslinking.

Purified PICV (50 µg) was treated with 5 µM TAMRA-conjugated Peptide 1 for 30 min at 37° C. The crosslinking agent bis-sulfosuccinimidyl suberate ($BS^3$) was added at concentrations of 0.5, 1, or 5 mM and incubated at RT for 30 min. The crosslinking reaction was quenched by addition of 50 mM Tris (pH 6.8) for 15 min at RT. Total protein was precipitated with 10% trichloroacetic acid overnight at 4° C. Protein was pelleted by centrifugation at 20,000×g for 15 min and washed with one volume of cold ethyl alcohol. SDS-PAGE was performed on a 4-10% Nuvex BIS-TRIS gel. Gels were imaged under UV light prior to fixation and colloidal Coomassie Blue staining.

Example 2

Evaluation of Antiviral Activity

Plaque Reduction Activity.

Figure 2:
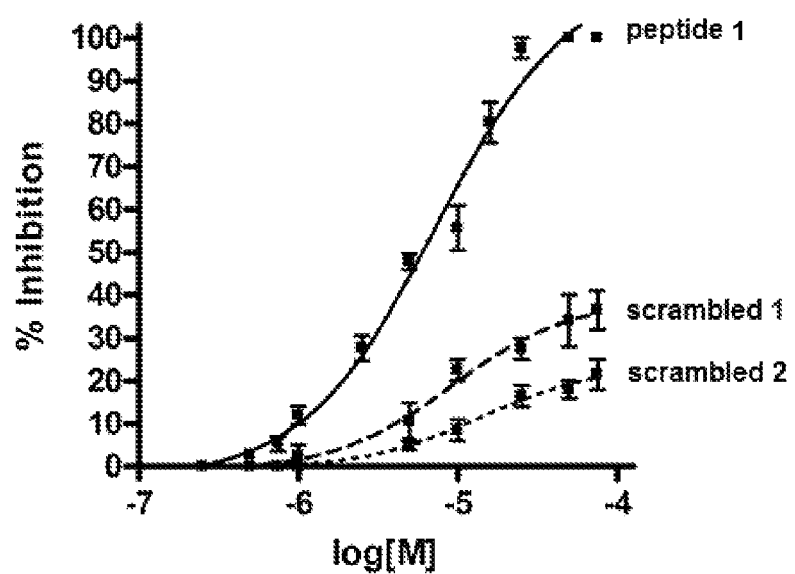
FIG. 2 provides dose-response curves for Peptide 1 and scrambled versions thereof.
Figure 3:
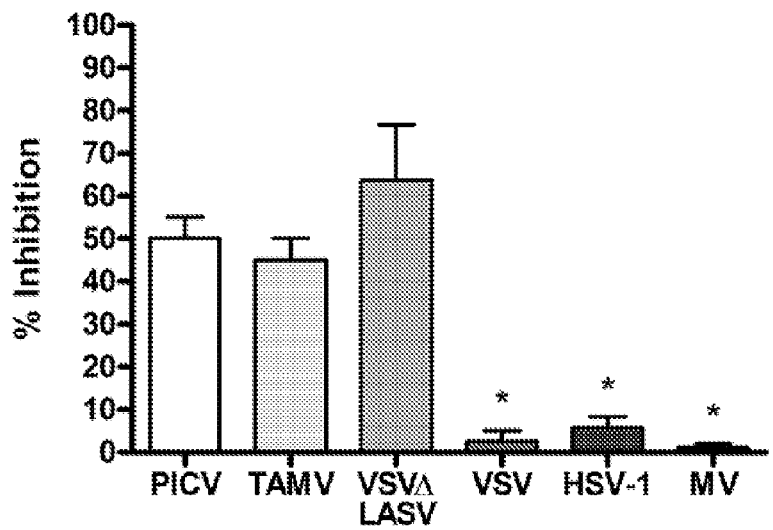
FIG. 3 is a histogram showing activity of Peptide 1 against various enveloped viruses at PICV $IC_{50}$.

Antiviral activity was assessed through plaque reduction assays as described in Example 1. Peptide 1 was determined to inhibit PICV with an $IC_{50}$ of 7.05±2.19 µM (FIG. 2). Complete inhibition of plaque formation occurred in the presence of approximately 20 µM peptide. Scrambled peptides demonstrated no significant inhibitory activity, suggesting that the antiviral mechanism of Peptide 1 is sequence-specific. For use under BSL-2 conditions, TAMV and VSVΔ-LASV were selected as representatives of New and Old World arenaviruses, respectively. Peptide 1 was effective at inhibiting both viruses, with plaque reduction of 45.0±5.0% for TAMV and 63.8±13.0% for VSVΔLASV observed at the $IC_{50}$ for PICV (FIG. 3). VSV, HSV-1, and MV were randomly selected to assess the breadth of peptide activity; however, plaque formation by these viruses was not significantly inhibited, indicating that activity is specific for arenaviruses. Peptides 2 through 7 (Table 1) were active but did not afford any significant improvement in activity relative to Peptide 1.

TABLE 1

| SEQ ID NO: | | | Sequence |
|---|---|---|---|
| 1 | PICV GP2 | | GFFTWDLSDSSGQHVPGGYCLEQWAIIWAGIKCFDNTVMAKCNKDHNEE FCDTMRLFDFNQNAIKTLQLNVENSLNLFKKTINGLISDSLVIRNSLKQLA KIPYCNYTKFWYINDTITGRHSLPQCWLVHNGSYLNETHFKNDWLWESQ NLYNEMLMKEYEERQGKTPLALTDICFWSLVFYTITVFLHIVGIPTHRHIIG DGCPKPHRITRNSLCSCGYYKYQRNLTNG |
| 2 | PICV GP2 Fusion Peptide | | GFFTWDLSDSSGQHVPGGY |
| 3 | PICV FIR | | SLKQLAKIPYCNYTKFWYINDTITGRHSLPQC |
| 4 | Peptide 1 | | LNLFKKTINGLISDSLVIR |
| 5 | Peptide 2 | | ENQLNLFKKTINGLISDSLVIR |
| 6 | Peptide 3 | | LNVENQLNLFKKTINGLISDSLVIR |
| 7 | Peptide 4 | | TLQLNVENSLNLFKKTINGLISDSLVIR |
| 8 | Peptide 5 | | QLNLFKKTINGLISDSLVIRNSL |

TABLE 1-continued

| SEQ ID NO: 9 | Peptide 6 | QLNLFKKTINGLISDSLVIRNSLKQL |
|---|---|---|
| SEQ ID NO: 10 | Peptide 7 | QLNLFKKTINGLISDSLVIRNSLKQLAKI |
| SEQ ID NO: 11 | Peptide 8 | PGGYALEQWAIIWAGIKAF |
| SEQ ID NO: 12 | Scrambled Peptide 1 | RTILLFIGVKDLLKNSNSI |
| SEQ ID NO: 13 | Scrambled Peptide 2 | KLTILNKDGILRSVILSFN |
| SEQ ID NO: 14 | Tamiami virus GP2 | SFFTWSLSDAVGNDMPGGYCLEKWMLVASQLKCFGNTAVAKCNLNHDS EFCDMLRLFDFNKKAIETLQNKTRSQLNIAINAINSLISDNLLMKNRIKELM DIPFCNYTKFWYVNHTKLNHHSLPRCWLVKNGSYLNESEFRNDWLLESD HLISEILSKEYEERQGRTPLSLVICFWSTLFYTASIFLHLIRIPTHRHITGEGC PKPHRLKADSTCACGLYKQKRRPLKWVKSN |
| SEQ ID NO 15 | Lassa virus GP2 | GTFTWTLSDSEGNATPGGYCLTRWMLIEAELKCFGNTAVAKCNEKHDEE FCDMLRLFDFNKQAISRLKSEAQMSIQLINKAVNALINDQLIMKNHLRDIM GIPYCNYSKYWYLNHTITGKTSLPKCWLVSNGSYLNETHFSDDIEQQADN MITEMLQKEYMERQGKTPLGLVDLFVFSTSFYLISIFLRLVKIPTHRHIVGK PCPKPHRLNHMGICSCGLYKQPGVPVRWKR |

Fusion Assay.

Figure 4:
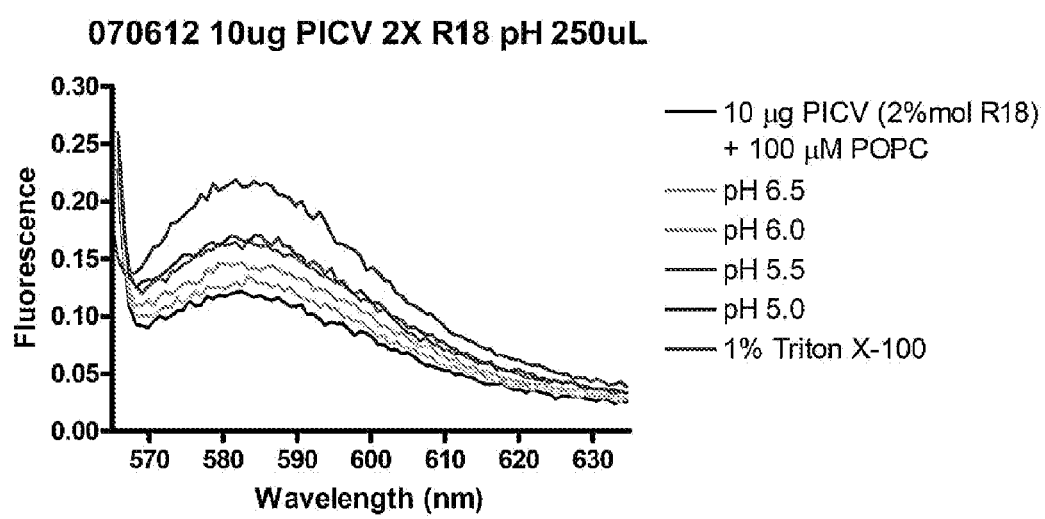
FIG. 4 is a line graph depicting pH-dependent dequenching of R18-labeled PICV.

In order to determine whether peptide-treated virions remain fusion-competent, purified PICV was labeled with octadecyl rhodamine (R18), the use of which has been well-established in bilayer-fusion assays. Use of the neutral lipid POPC is widely accepted for approximating biological membranes. Untreated R18-labeled virus exhibited approximately 52% dequenching following acidification to pH 5.0, with the highest rates of fusion occurring between pH 6.5-5.5 (FIG. 4). The kinetics of PICV dequenching are consistent with the results of di Simone et al. for LCMV fusion. Extending incubation time at each incremental pH decrease did not affect the extent of dequenching. When Peptide 1 was incubated with R18-labeled virus, extensive dequenching in the sample at pH 7.4, prior to the addition of LUVs or acid was observed.

Figures 5, 6:
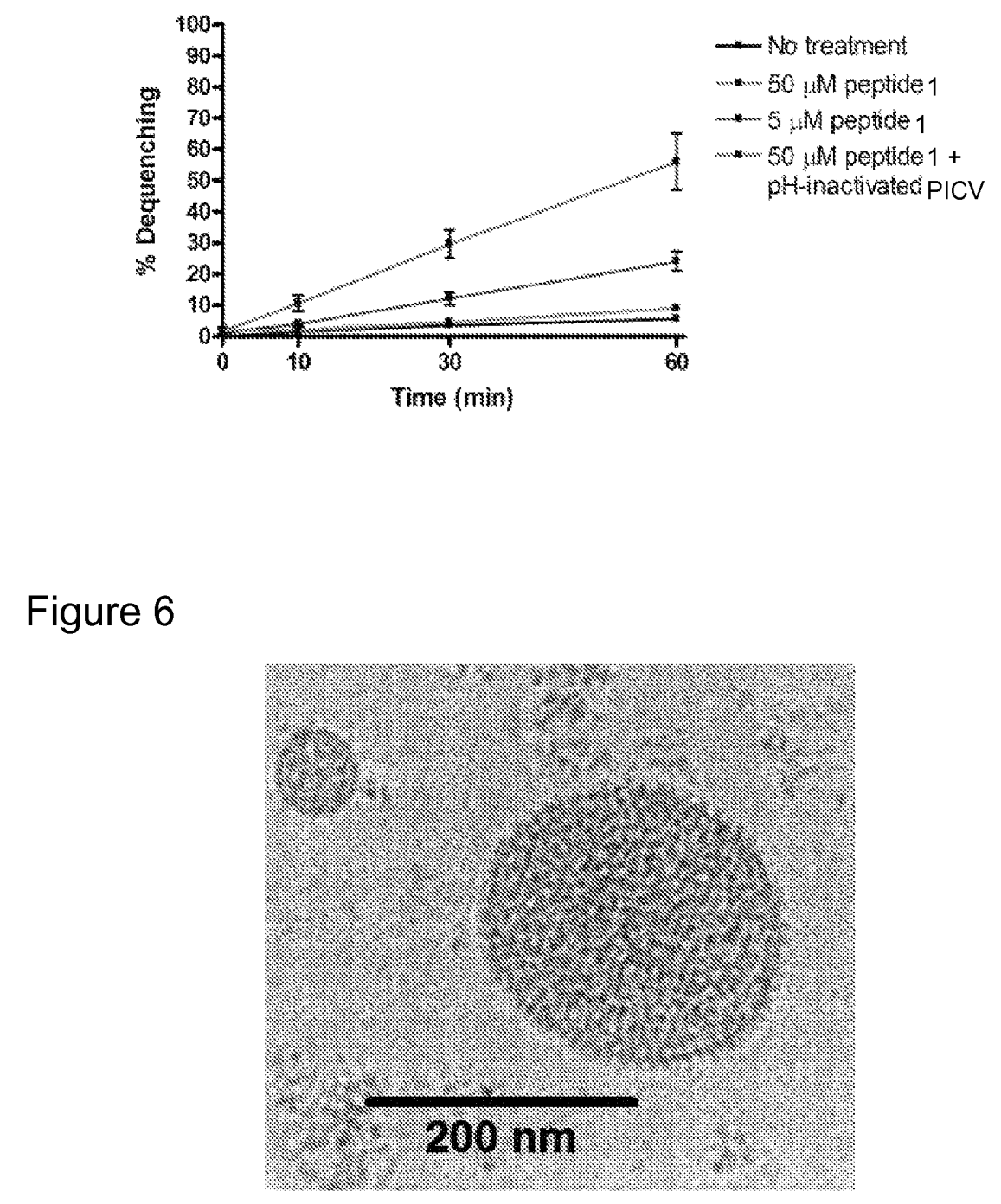

Concentration-dependent dequenching of labeled PICV occurred at a consistent rate following addition of peptide (FIG. 5). Labeled virus incubated with LUVs and 5 or 50 µM peptide exhibited approximately 24 or 54% dequenching, respectively, after 1 h. The R18 label is stable once incorporated into viral membranes, with only 5% leakage over the duration of the experiment. Peptide 1 did not induce significant dequenching of PICV pre-incubated at pH 5.0 prior to labeling, indicating that the peptide itself does not directly cause fusion of lipid bilayers and that dequenching by Peptide 1 is strictly glycoprotein-mediated.

Cryo-Electron Microscopy.

Figure 7:
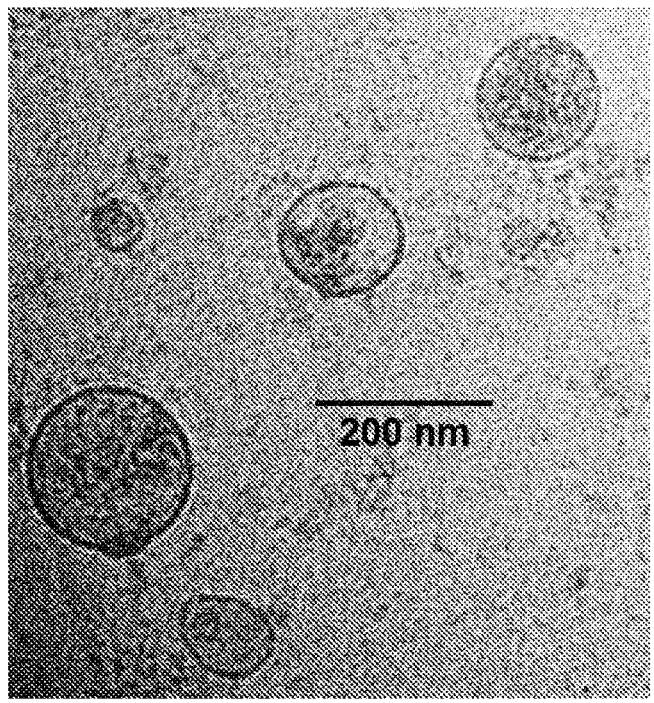
FIG. 7 is a cryo-electron micrograph of PICV at pH 5.0.
Figure 8:
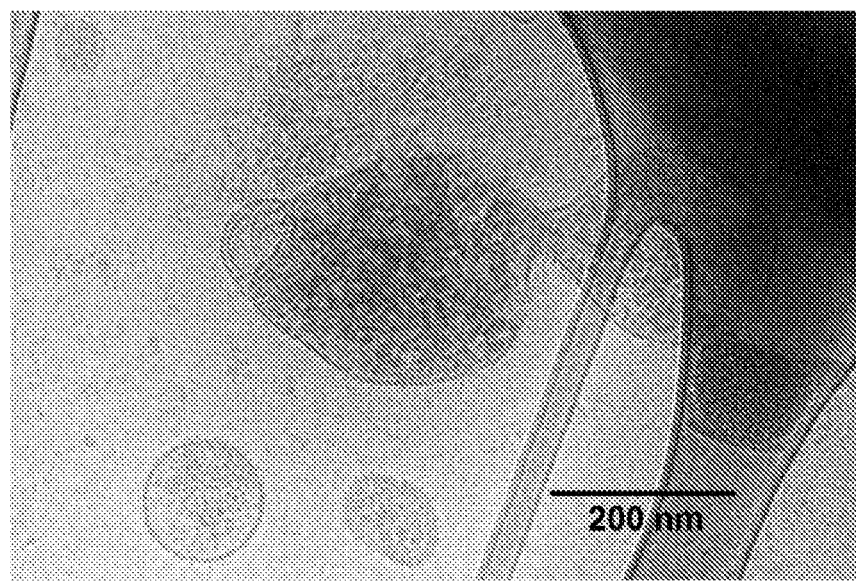
FIG. 8 is a cryo-electron micrograph of Peptide 1-treated PICV.
Figure 9:
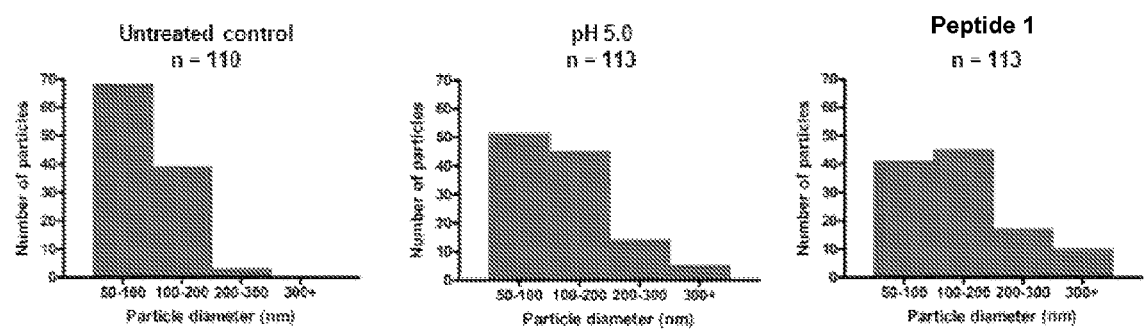
FIG. 9 is a series of histograms showing size distribution of viral particles; control (left), pH 5 (middle), and Peptide 1 (right).
Figure 10:
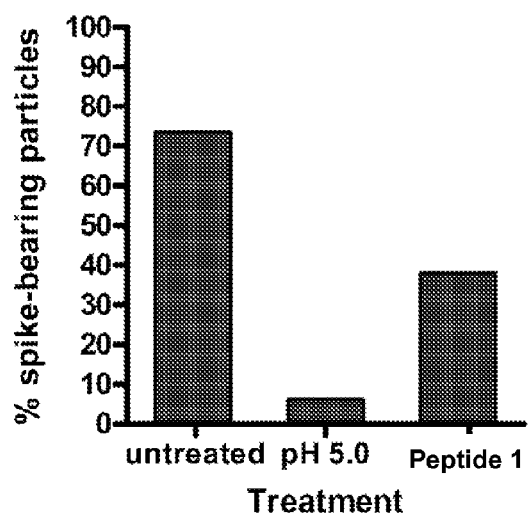
FIG. 10 is a histogram illustrating presence of pre-fusion glycoprotein spikes following treatment.

Viral morphology was assessed by cryo-EM following treatment. Untreated control samples showed pleiomorphic (80-250 nm in diameter), spherical virions with distinct glycoprotein spikes (FIG. 6). Incubation at pH 5.0 resulted in the formation of particles lacking visible glycoprotein spikes (FIG. 7). Loss of the pre-fusion spike structure is indicative of GP1 dissociation. Reorganization of the internal viral protein matrix in acidified influenza virions has been demonstrated by Fontana et al., and this may explain the post-fusion radial asymmetry observed in some PICV particles. As seen in histograms, low pH-treated virions show a trend toward larger particles versus untreated PICV, which is consistent with fusion among virions (FIG. 9). Viral samples treated with Peptide 1 displayed considerable similarity to those exposed to low pH (FIG. 8). Peptide-treated PICV demonstrated a greater shift toward larger particles, suggesting more extensive fusion with peptide than with acidification. Disappearance of pre-fusion glycoprotein spikes was also observed in a significant number of particles incubated with peptide, but the phenomenon is less extensive than with low pH (FIG. 10).

Steady-State Fluorescence Anisotropy Assay.

Figure 12:
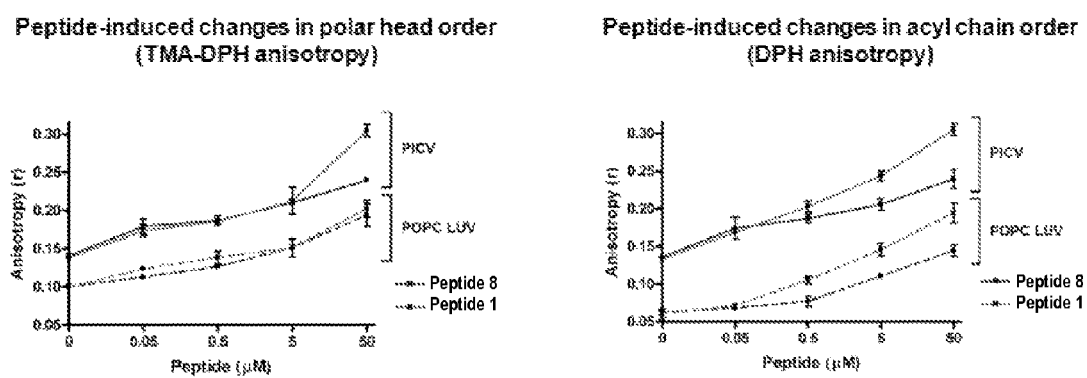
FIG. 12 compares line graphs showing lipid probe steady-state anisotropy assays; TMA-DPH (left); DPH (right).

In order to investigate whether Peptide 1 interacts with membranes, the fluorescent lipid probes DPH and TMA-DPH were used to monitor lipid order/packing. Another GP2-derived antiviral peptide, Peptide 8 (SEQ ID NO: 11), which overlaps with a portion of the fusion peptide region, was used as a comparison, since it binds to the surface of membranes. Anisotropy values of TMA-DPH increased substantially upon addition of Peptide 1, indicating increased rigidity or tighter packing at the interface (FIG. 12). This suggests that the peptide does, in fact, interact with membranes. Higher anisotropy values were associated only with higher concentrations (5-50 µM) of peptide. DPH was used to investigate the extent of peptide-induced perturbance in the membrane, since it accumulates in the bilayer core, whereas TMA-DPH is anchored just below the bilayer surface. Concentration-dependent increases in probe anisotropy values were observed to a greater degree with Peptide 1 than with Peptide 8, which is responsible for purely incidental alterations in acyl chain packing. These results suggest that Peptide 1 inserts deeply into both model and viral membranes.

Crosslinking.

Figure 11:
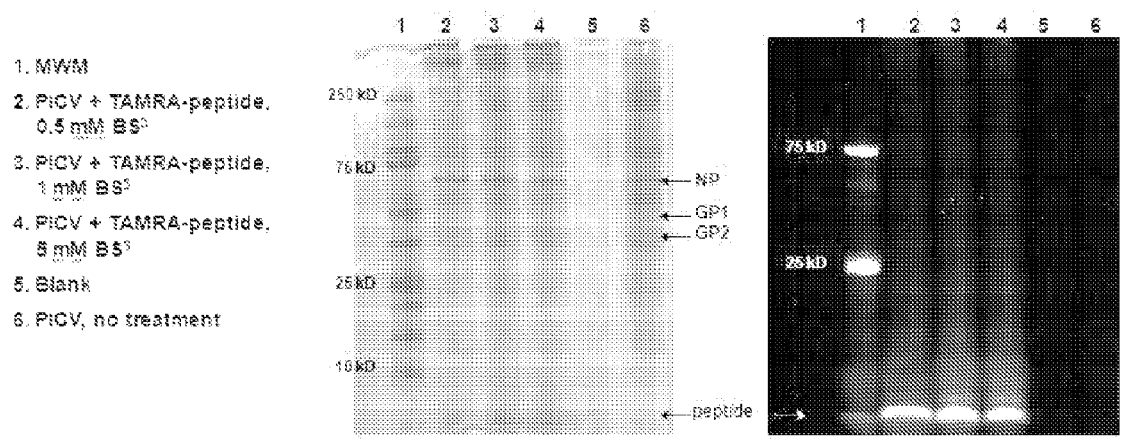
FIG. 11 illustrates the results after crosslinking by $BS^3$ following TAMRA-peptide treatment.

To determine the extent to which Peptide 1 interacts directly with glycoprotein spikes, purified virus was incubated with a TAMRA-conjugated peptide prior to crosslinking by $BS^3$. TAMRA is UV-visible at low-picogram quantities, making the assay highly sensitive to peptide-glycoprotein binding. The crosslinking agent $BS^3$ acts on primary amines and does not cross membranes. Oligomers of the peptide are observed, as are glycoprotein oligomers, after $BS^3$ treatment (FIG. 11). However, no interaction is observed between peptide and either monomeric or oligomeric glycoproteins. Additionally, crosslinking by glutaraldehyde failed to reveal peptide-glycoprotein binding.

Orphan Plaque Assays.

Figure 13:
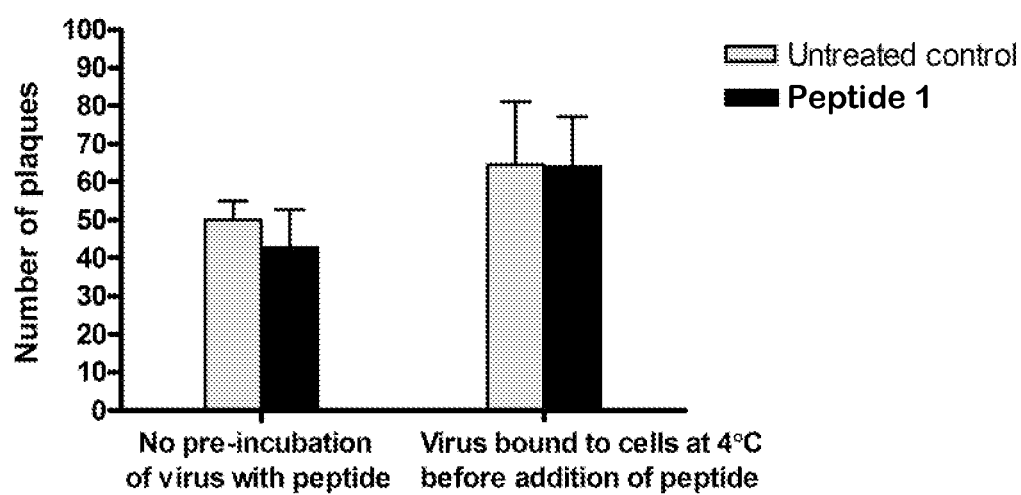
FIG. 13 is a histogram showing the effect of peptide treatment on viral infectivity.

In order to verify that Peptide 1 does not enhance viral infectivity, monolayers were exposed to PICV and peptide together without pre-incubation for 1 h. Although peptide activity is not as high as when virus is treated prior to incubation with cells, no increase in plaque number was observed (FIG. 13). Virus was also incubated 1 h with cells at 4° C., which enables binding without internalization, prior to addition of virus for 1 h at 37° C. Again, no significant antiviral activity or increase in viral infectivity was observed versus the control.

Three additional peptides were tested which showed no significant antiviral activity; i.e., (a) residues 110-128 of SEQ ID NO: 1 including substitution C126A; (b) residues 140-157 of SEQ ID NO: 1; and (c) residues 174-192 including substitution C175A. These results in combination with the results of the other peptides disclosed herein indicate that the active region for viral inhibition resides in approximately residues 1-105 of the GP2 protein.

Discussion

In vitro assays reveal specific antiviral activity in the low micromolar range, and its efficacy extends to both New and Old World arenaviruses. Peptide 1 was initially identified using Membrane Protein eXplorer, which employs an algorithm based upon the Wimley-White Interfacial Hydropathy Scale (WWIHS). GPC regions likely to be involved in protein-protein or protein-lipid interface formation likely also possess high WWIHS scores. WWIHS has been used previously to design inhibitory peptides for range of enveloped viruses. These peptides appear to possess diverse mechanisms of action, including stabilization of fusion protein conformers, viral membrane disruption, and viral genome expulsion. The findings implicate premature fusion protein refolding as an additional mode of viral inactivation.

Peptides derived from CHR typically show greater inhibitory activity than NHR; this may stem partly from the greater tendency of peptides from NHR to oligomerize since they form the 6-HB core; a peptide originating from the PICV CHR exhibited no significant antiviral activity at 100 µM. Mild perturbance due to heat, pH, pressure, or denaturants has been shown to trigger fusogenic reorganization of viral glycoproteins. These various triggers can act directly on glycoprotein ectodomains to lower the kinetic barrier between the metastable pre-fusion conformation and the thermodynamically-stable post-fusion conformation.

Once fusion proteins are activated, the fusogenic rearrangement is thought to be completed within approximately 20 seconds. The slower rate of peptide-induced activation may account for more extensive fusion, as evidenced by the larger particles created by peptide treatment versus low pH. Interestingly, Peptide 1 did not enhance infectivity of PICV, even when the virus was allowed to bind to cells before the addition of peptide. This may stem from the slowness of inactivation by peptide compared with endocytosis.

The triggering of its glycoprotein spikes leaves a virion unable to bind its cellular receptor, since GP1 must dissociate prior to the GP2 conformational rearrangement. Further, endosomal escape would be impeded for virions with some or all of their glycoproteins already deployed, since pore formation requires engagement of a minimum number of spikes at the locus.

The effectiveness of a bilayer-perturbing peptide against PICV, TAMV, and VSVΔLASV, but not VSV, HSV-1, or MV bears closer inspection. A nominal level of bilayer fluidity is necessary for formation of fusion pores. Agents that increase rigidity in viral and/or cellular membranes are known to hamper fusion. Although differences in membrane lipid composition could account for the differences in peptide activity against viruses as disparate as PICV and VSV, they do not account for the inactivation of VSV-LASV but not VSV.

Substantial increases in DPH and TMA-DPH anisotropy values were observed only at pharmacologically-relevant peptide concentrations (concentrations that produced significant antiviral activity). This observation suggests that membrane perturbance directly relates to peptide mechanism of action.

Unlike most fusion protein spikes, which have three transmembrane domains, the mature arenavirus spike possesses nine transmembrane domains. This association of bilayer-spanning helices may render arenaviruses uniquely sensitive to membrane-perturbing agents. GP2-SSP interaction is required for fusion-competence. Point mutations in SSP transmembrane domains can result in viral hypo- or hyperfusogenicity. SSP may stabilize GP2.

REFERENCES

The following references are incorporated herein by reference in their entirety.

Chu V C, McElroy L J, Chu V, Bauman B E, Whitaker G R. The avian coronavirus infectious bronchitis virus undergoes direct low-pH-dependent fusion activation during entry into host cells. J Virol 80:7 (2006) 3180-3188.

Jones P L, Korte T, Blumenthal R. Conformational changes in cell surface HIV-1 envelope glycoproteins are triggered by cooperation between cell surface CD4 and co-receptors. J Biol Chem 273:1 (1988) 404-409.

Hoekstra D, de Boer T, Klappe K, Wilschut J. Fluorescence method for measuring the kinetics of fusion between biological membranes. Biochemistry 23 (1984) 5675-5681.

Di Simone C, Zandonatti M A, Buchmeier M J. Acidic pH triggers LCMV membrane fusion activity and conformational change in the glycoprotein spike. Virology 198 (1994) 455-465.

Wimley W C, White S H. Experimentally determined hydrophobicity scale for proteins at membrane interfaces. Nat Struct Biol 3 (1996) 842-848.

Weber G, Lawerence D J R. Fluorescent indicators of adsorption in aqueous solution and on the solid phase. Biochem J 56 (325th Meeting):xxxi (1954).

Neuman B W, Adair B D, Burns J W, Milligan R A, Buchmeier M J, Yeager M. Complementarity in the supramolecular design of arenaviruses and retroviruses revealed by electron cryomicroscopy and image analysis. J Virol 79:6 (2005) 3822-3830.

Neuman B W, Adair B D, Yeager M, Buchmeier M J. Purification and electron microscopy of coronavirus particles. Methods Mol Biol 454 (2008) 129-136.

Eschli B, Quirin K, Wepf A, Weber J, Zinkernagel R M, Hengartner H. Identification of an N-terminal trimeric coiled-coil core within arenavirus glycoprotein 2 permits assignment to class I fusion proteins. J Virol 80 (2006) 5897-5907.

NIAID. NIAID biodefense research agenda for CDC category A agents. NIH publication no. 03-5308, NIH, Bethesda, Md. (2002).

Carr C M, Chaudhry C, Kim P S. Influenza hemagglutinin is spring-loaded by a metastable native conformation. Proc Natl Acad Sci USA 94:26 (1997) 14306-14313.

Gaspar L P, Silva A C B, Gomes A M O, Freitas M S, Ano Bom A P D, Schwarcz W D, Mestecky J, Novak M J, Foguel D, Silva J L. Hydrostatic pressure induces the fusion-active state of enveloped viruses. J Biol Chem 277: 10 (2002) 8433-8439.

Sainz B Jr, Mossel E C, Gallaher W R, Peters C J, Wilson R B, Garry R F. Inhibition of severe acute respiratory syndrome-associated coronavirus (SARS-CoV) infectivity by peptides analogous to the viral spike protein. Virus Res 120: 1-2 (2006) 146-155.

Hrobowski Y M, Garry R F, Michael S F. Peptide inhibitors of dengue virus and West Nile Virus infectivity. Virol J 2:49 (2005).

We claim:

1. An isolated arenavirus fusion inhibiting (AVI) peptide consisting of a 19 to 50 consecutive amino acid residue segment of SEQ ID NO: 1 from the region of residues 1 to 105 thereof; wherein optionally, a cysteine residue of the segment of SEQ ID NO: 1 is replaced by an alanine residue, and optionally, a serine residue of the segment of SEQ ID NO: 1 is replaced by a glutamine residue, wherein the segment includes at least consecutive residues 75 to 93 of SEQ ID NO: 1.

2. An isolated arenavirus fusion inhibiting (AVI) peptide consisting of 15 to 20 consecutive amino acid residues from the region of residues 1 to 105 of SEQ ID NO: 1 or SEQ ID NO: 14.

3. The arenavirus fusion inhibiting peptide of claim 1 wherein the peptide consists of SEQ ID NO: 4.

4. The arenavirus fusion inhibiting peptide of claim 1 wherein the peptide consists of a sequence selected from the group consisting of SEQ ID NO: 5 to SEQ ID NO: 10, inclusive.

5. The arenavirus fusion inhibiting peptide of claim 1 wherein the peptide inhibits viral fusion of an arenavirus selected from Pichinde virus, Tamiami virus, and Lassa virus.

6. An isolated arenavirus fusion inhibiting peptide consisting of 15 to 20 consecutive amino acid residues of SEQ ID NO: 1, SEQ ID NO: 14, or SEQ ID NO: 15 from the region of residues 1 to 105 thereof and including at least one amino acid substitution selected from (a) an alanine residue in place of a cysteine residue and (b) a glutamine residue in place of a serine residue.

7. The arenavirus fusion inhibiting peptide of claim 6 wherein the peptide includes at least consecutive residues 75 to 93 of SEQ ID NO: 1 and comprises at least one substitution of a glutamine residue in place of a serine residue.

8. A pharmaceutical composition comprising the arenavirus fusion inhibiting peptide of claim 1 in a pharmaceutically acceptable carrier.

9. The pharmaceutical composition of claim 8 wherein the pharmaceutically acceptable carrier comprises an aqueous buffer at a pH of about 6.5 to 7.5.

10. The pharmaceutical composition of claim 8 wherein the pharmaceutically acceptable carrier comprises physiological saline solution.

11. The pharmaceutical composition of claim 8 wherein the pharmaceutically acceptable carrier comprises phosphate buffered saline.

12. The pharmaceutical composition of claim 8 wherein the pharmaceutically acceptable carrier comprises a buffer salt and the composition is a spray dried or lyophilized powder.

13. A pharmaceutical composition comprising the arenavirus fusion inhibiting peptide of claim 2 in a pharmaceutically acceptable carrier.

14. A pharmaceutical composition comprising the arenavirus fusion inhibiting peptide of claim 6 in a pharmaceutically acceptable carrier.

15. A method of treating an arenavirus infection comprising administering in a pharmaceutically acceptable carrier an effective amount of the isolated arenavirus fusion inhibiting peptide of claim 1 to a subject.

16. The method of claim 15 wherein the peptide consists of a sequence selected from the group consisting of SEQ ID NO: 4 through SEQ ID NO: 10, inclusive.

17. A method of treating an arenavirus infection comprising administering in a pharmaceutically acceptable carrier an effective amount of the isolated arenavirus fusion inhibiting peptide of claim 2 to a subject.

18. A method of treating an arenavirus infection comprising administering in a pharmaceutically acceptable carrier an effective amount of the isolated arenavirus fusion inhibiting peptide of claim 6 to a subject.

19. The method of claim 18 wherein the peptide consists of SEQ ID NO: 11.

20. The arenavirus fusion inhibiting peptide of claim 6 wherein the peptide consists of SEQ ID NO: 11.

* * * * *

SEQUENCE LISTING

```
<160> NUMBER OF SEQ ID NOS: 15

<210> SEQ ID NO 1
<211> LENGTH: 230
<212> TYPE: PRT
<213> ORGANISM: Pichinde Virus

<400> SEQUENCE: 1

Gly Phe Phe Thr Trp Asp Leu Ser Asp Ser Ser Gly Gln His Val Pro
1               5                   10                  15

Gly Gly Tyr Cys Leu Glu Gln Trp Ala Ile Ile Trp Ala Gly Ile Lys
            20                  25                  30

Cys Phe Asp Asn Thr Val Met Ala Lys Cys Asn Lys Asp His Asn Glu
        35                  40                  45

Glu Phe Cys Asp Thr Met Arg Leu Phe Asp Phe Asn Gln Asn Ala Ile
    50                  55                  60

Lys Thr Leu Gln Leu Asn Val Glu Asn Ser Leu Asn Leu Phe Lys Lys
65                  70                  75                  80

Thr Ile Asn Gly Leu Ile Ser Asp Ser Leu Val Ile Arg Asn Ser Leu
                85                  90                  95

Lys Gln Leu Ala Lys Ile Pro Tyr Cys Asn Tyr Thr Lys Phe Trp Tyr
            100                 105                 110

Ile Asn Asp Thr Ile Thr Gly Arg His Ser Leu Pro Gln Cys Trp Leu
        115                 120                 125

Val His Asn Gly Ser Tyr Leu Asn Glu Thr His Phe Lys Asn Asp Trp
    130                 135                 140

Leu Trp Glu Ser Gln Asn Leu Tyr Asn Glu Met Leu Met Lys Glu Tyr
145                 150                 155                 160

Glu Glu Arg Gln Gly Lys Thr Pro Leu Ala Leu Thr Asp Ile Cys Phe
                165                 170                 175

Trp Ser Leu Val Phe Tyr Thr Ile Thr Val Phe Leu His Ile Val Gly
            180                 185                 190

Ile Pro Thr His Arg His Ile Ile Gly Asp Gly Cys Pro Lys Pro His
        195                 200                 205

Arg Ile Thr Arg Asn Ser Leu Cys Ser Cys Gly Tyr Tyr Lys Tyr Gln
    210                 215                 220

Arg Asn Leu Thr Asn Gly
225                 230

<210> SEQ ID NO 2
<211> LENGTH: 19
<212> TYPE: PRT
<213> ORGANISM: Pichinde virus

<400> SEQUENCE: 2

Gly Phe Phe Thr Trp Asp Leu Ser Asp Ser Ser Gly Gln His Val Pro
1               5                   10                  15

Gly Gly Tyr

<210> SEQ ID NO 3
<211> LENGTH: 32
<212> TYPE: PRT
<213> ORGANISM: Pichinde virus
```

```
<400> SEQUENCE: 3

Ser Leu Lys Gln Leu Ala Lys Ile Pro Tyr Cys Asn Tyr Thr Lys Phe
1               5                   10                  15

Trp Tyr Ile Asn Asp Thr Ile Thr Gly Arg His Ser Leu Pro Gln Cys
            20                  25                  30

<210> SEQ ID NO 4
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 4

Leu Asn Leu Phe Lys Lys Thr Ile Asn Gly Leu Ile Ser Asp Ser Leu
1               5                   10                  15

Val Ile Arg

<210> SEQ ID NO 5
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 5

Glu Asn Gln Leu Asn Leu Phe Lys Lys Thr Ile Asn Gly Leu Ile Ser
1               5                   10                  15

Asp Ser Leu Val Ile Arg
            20

<210> SEQ ID NO 6
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 6

Leu Asn Val Glu Asn Gln Leu Asn Leu Phe Lys Lys Thr Ile Asn Gly
1               5                   10                  15

Leu Ile Ser Asp Ser Leu Val Ile Arg
            20                  25

<210> SEQ ID NO 7
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 7

Thr Leu Gln Leu Asn Val Glu Asn Ser Leu Asn Leu Phe Lys Lys Thr
1               5                   10                  15

Ile Asn Gly Leu Ile Ser Asp Ser Leu Val Ile Arg
            20                  25

<210> SEQ ID NO 8
<211> LENGTH: 23
<212> TYPE: PRT
<213> ORGANISM: Artificial Sequence
<220> FEATURE:
<223> OTHER INFORMATION: Synthetic Peptide
```

-continued

<400> SEQUENCE: 8

Gln Leu Asn Leu Phe Lys Lys Thr Ile Asn Gly Leu Ile Ser Asp Ser
1               5                   10                  15

Leu Val Ile Arg Asn Ser Leu
            20

<210> SEQ ID NO 9
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 9

Gln Leu Asn Leu Phe Lys Lys Thr Ile Asn Gly Leu Ile Ser Asp Ser
1               5                   10                  15

Leu Val Ile Arg Asn Ser Leu Lys Gln Leu
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 10

Gln Leu Asn Leu Phe Lys Lys Thr Ile Asn Gly Leu Ile Ser Asp Ser
1               5                   10                  15

Leu Val Ile Arg Asn Ser Leu Lys Gln Leu Ala Lys Ile
            20                  25

<210> SEQ ID NO 11
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 11

Pro Gly Gly Tyr Ala Leu Glu Gln Trp Ala Ile Ile Trp Ala Gly Ile
1               5                   10                  15

Lys Ala Phe

<210> SEQ ID NO 12
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 12

Arg Thr Ile Leu Leu Phe Ile Gly Val Lys Asp Leu Leu Lys Asn Ser
1               5                   10                  15

Asn Ser Ile

<210> SEQ ID NO 13
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 13

```
Lys Leu Thr Ile Leu Asn Lys Asp Gly Ile Leu Arg Ser Val Ile Leu
1               5                   10                  15

Ser Phe Asn

<210> SEQ ID NO 14
<211> LENGTH: 233
<212> TYPE: PRT
<213> ORGANISM: Tamiami virus

<400> SEQUENCE: 14

Ser Phe Phe Thr Trp Ser Leu Ser Asp Ala Val Gly Asn Asp Met Pro
1               5                   10                  15

Gly Gly Tyr Cys Leu Glu Lys Trp Met Leu Val Ala Ser Gln Leu Lys
            20                  25                  30

Cys Phe Gly Asn Thr Ala Val Ala Lys Cys Asn Leu Asn His Asp Ser
        35                  40                  45

Glu Phe Cys Asp Met Leu Arg Leu Phe Asp Phe Asn Lys Lys Ala Ile
    50                  55                  60

Glu Thr Leu Gln Asn Lys Thr Arg Ser Gln Leu Asn Ile Ala Ile Asn
65                  70                  75                  80

Ala Ile Asn Ser Leu Ile Ser Asp Asn Leu Met Lys Asn Arg Ile
                85                  90                  95

Lys Glu Leu Met Asp Ile Pro Phe Cys Asn Tyr Thr Lys Phe Trp Tyr
                100                 105                 110

Val Asn His Thr Lys Leu Asn His His Ser Leu Pro Arg Cys Trp Leu
            115                 120                 125

Val Lys Asn Gly Ser Tyr Leu Asn Glu Ser Glu Phe Arg Asn Asp Trp
        130                 135                 140

Leu Leu Glu Ser Asp His Leu Ile Ser Glu Ile Leu Ser Lys Glu Tyr
145                 150                 155                 160

Glu Glu Arg Gln Gly Arg Thr Pro Leu Ser Leu Val Ile Cys Phe Trp
                165                 170                 175

Ser Thr Leu Phe Tyr Thr Ala Ser Ile Phe Leu His Leu Ile Arg Ile
                180                 185                 190

Pro Thr His Arg His Ile Thr Gly Glu Gly Cys Pro Lys Pro His Arg
            195                 200                 205

Leu Lys Ala Asp Ser Thr Cys Ala Cys Gly Leu Tyr Lys Gln Lys Arg
        210                 215                 220

Arg Pro Leu Lys Trp Val Lys Ser Asn
225                 230

<210> SEQ ID NO 15
<211> LENGTH: 232
<212> TYPE: PRT
<213> ORGANISM: Lassa virus

<400> SEQUENCE: 15

Gly Thr Phe Thr Trp Thr Leu Ser Asp Ser Glu Gly Asn Ala Thr Pro
1               5                   10                  15

Gly Gly Tyr Cys Leu Thr Arg Trp Met Leu Ile Glu Ala Glu Leu Lys
            20                  25                  30

Cys Phe Gly Asn Thr Ala Val Ala Lys Cys Asn Glu Lys His Asp Glu
        35                  40                  45

Glu Phe Cys Asp Met Leu Arg Leu Phe Asp Phe Asn Lys Gln Ala Ile
    50                  55                  60
```

```
Ser Arg Leu Lys Ser Glu Ala Gln Met Ser Ile Gln Leu Ile Asn Lys
 65          70                  75                  80

Ala Val Asn Ala Leu Ile Asn Asp Gln Leu Ile Met Lys Asn His Leu
                 85                  90                  95

Arg Asp Ile Met Gly Ile Pro Tyr Cys Asn Tyr Ser Lys Tyr Trp Tyr
            100                 105             110

Leu Asn His Thr Ile Thr Gly Lys Thr Ser Leu Pro Lys Cys Trp Leu
        115             120                 125

Val Ser Asn Gly Ser Tyr Leu Asn Glu Thr His Phe Ser Asp Asp Ile
    130             135                 140

Glu Gln Gln Ala Asp Asn Met Ile Thr Glu Met Leu Gln Lys Glu Tyr
145             150             155                 160

Met Glu Arg Gln Gly Lys Thr Pro Leu Gly Leu Val Asp Leu Phe Val
            165             170                 175

Phe Ser Thr Ser Phe Tyr Leu Ile Ser Ile Phe Leu Arg Leu Val Lys
            180             185             190

Ile Pro Thr His Arg His Ile Val Gly Lys Pro Cys Pro Lys Pro His
        195             200             205

Arg Leu Asn His Met Gly Ile Cys Ser Cys Gly Leu Tyr Lys Gln Pro
    210             215             220

Gly Val Pro Val Arg Trp Lys Arg
225             230
```